US009307947B2

(12) United States Patent
Taguchi et al.

(10) Patent No.: US 9,307,947 B2
(45) Date of Patent: Apr. 12, 2016

(54) IMAGE DIAGNOSTIC APPARATUS AND METHOD OF CONTROLLING THE SAME

(75) Inventors: Hiroki Taguchi, Otawara (JP); Masaharu Tsuyuki, Nasushiobara (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 624 days.

(21) Appl. No.: 13/613,266

(22) Filed: Sep. 13, 2012

(65) Prior Publication Data

US 2013/0012814 A1 Jan. 10, 2013

Related U.S. Application Data

(63) Continuation of application No. PCT/JP2011/075399, filed on Nov. 4, 2011.

(30) Foreign Application Priority Data

Nov. 5, 2010 (JP) .................................. 2010-247967

(51) Int. Cl.
 A61B 6/00 (2006.01)
 A61B 5/055 (2006.01)
 A61B 5/00 (2006.01)

(52) U.S. Cl.
 CPC .............. *A61B 6/481* (2013.01); *A61B 6/469* (2013.01); *A61B 6/486* (2013.01); *A61B 6/488* (2013.01); *A61B 6/541* (2013.01); *A61B 5/0037* (2013.01); *A61B 5/055* (2013.01)

(58) Field of Classification Search
 CPC .... A61B 5/7285; A61B 5/7289; A61B 6/032; A61B 6/504; A61B 6/484; A61B 6/00; A61B 6/486; A61B 6/481; A61B 5/055; A61B 6/649; A61B 6/488; A61B 6/541; G01R 33/5673; G01R 33/5601; G01R 33/5676; G01S 7/52039
 See application file for complete search history.

(56) References Cited

U.S. PATENT DOCUMENTS 5,784,488 A * 7/1998 Kuwata .............. H04N 1/40062
 358/3.21
2003/0076920 A1 * 4/2003 Shinno .................... A61B 6/032
 378/4
2003/0206647 A1 * 11/2003 Yamamichi .............. G06K 9/03
 382/128

(Continued)

FOREIGN PATENT DOCUMENTS

JP 06-114049 A 4/1994
JP 2008-014813 A 1/2008

(Continued)

OTHER PUBLICATIONS

English translation of the international preliminary report on patentability mailed on May 16, 2013 for corresponding International Application No. PCT/JP2011/75399.

*Primary Examiner* — Amanda Lauritzen Moher
(74) *Attorney, Agent, or Firm* — Yoshida & Associates, LLC

(57) ABSTRACT

An image diagnostic apparatus of an embodiment includes a density change acquisition unit, a trigger generating unit and a control unit. The density change acquisition unit is configured to acquire data corresponding to a temporal change in density of a contrast agent injected into an object. The trigger generating unit is configured to generate a trigger when abnormal data has been detected by a first threshold processing of the data. The trigger is generated by a second threshold processing of data other than the abnormal data. The control unit is configured to perform a control of contrast imaging for the object based on the trigger.

7 Claims, 4 Drawing Sheets

(56) References Cited

U.S. PATENT DOCUMENTS

2010/0114064 A1* 5/2010 Kalafut et al. ............... 604/508
2010/0254509 A1* 10/2010 Sugaya .................. A61B 6/032
378/16

FOREIGN PATENT DOCUMENTS

| JP | 2010-213760 A | 9/2010 |
| WO | 2010/064727 A1 | 6/2010 |

* cited by examiner

IMAGE DIAGNOSTIC APPARATUS AND METHOD OF CONTROLLING THE SAME

CROSS REFERENCE TO RELATED APPLICATIONS

This is a continuation of Application PCT/JP2011/75399, filed Nov. 4, 2011.

This application is based upon and claims the benefit of priority from Japanese Patent Application No. 2010-247967, filed Nov. 5, 2010; the entire contents of which are incorporated herein by reference.

FIELD

Embodiments described herein relate generally to an image diagnostic apparatus and a method of controlling an image diagnostic apparatus.

BACKGROUND

Contrast imaging has been conducted by X-ray CT (Computed Tomography) scanner, which requires injection of a contrast agent into an object. In this contrast imaging, it is required in advance to decide an acquisition time at which an imaging scan is performed after injecting the contrast agent. For such a decision, changes in the CT value within a ROI (Region Of Interest) are monitored contrast agent injected into an object. The imaging scan is started at a time when the CT value within the ROI has reached a predetermined threshold. That is, this time is used as triggering timing for the imaging scan.

PRIOR TECHNICAL LITERATURE

[Patent literature 1] JPA-H6-114049

However, the conventional contrast imaging with the X-ray CT scanner is confronted with a drawback concerning with setting the triggering timing. Practically, in cases where objects such as X-ray high absorbers are present within a ROI for which CT value changes are monitored or in the proximity of such a ROI, the CT value will rise irrespective of densities of the contrast agent. This rise in the CT value may result in erroneous setting of the triggering timing for starting the imaging scan.

This fact is true of contrast agent carried out using a magnetic resonance imaging (MRI) apparatus. Concretely the MRI apparatus is used to monitor signal values depending on densities of a contrast agent in a ROI and decide data acquisition timing from the monitored signal values. In this case, artifacts may raise the signal values, which results in erroneously setting data acquisition timing.

Moreover, various types of control are required, for example, for changing imaging modes depending on densities of a contrast agent. In such a situation, it is important to properly set control timing without being influenced by occurrence of artifacts.

An object of the present invention is to provide an image diagnostic apparatus and a method of controlling the same, which can set more accurately control timing of a scan in the contrast imaging depending on densities of a contrast agent.

DETAILED DESCRIPTION

In general, according to one embodiment, an image diagnostic apparatus includes a density change acquisition unit, a trigger generating unit and a control unit. The density change acquisition unit is configured to acquire data corresponding to a temporal change in density of a contrast agent injected into an object. The trigger generating unit is configured to generate a trigger when abnormal data has been detected by a first threshold processing of the data. The trigger is generated by a second threshold processing of data other than the abnormal data. The control unit is configured to perform a control of contrast imaging for the object based on the trigger.

Further, according to one embodiment, a method of controlling an image diagnostic apparatus includes: acquiring data corresponding to a temporal change in density of a contrast agent injected into an object; generating a trigger when abnormal data has been detected by a first threshold processing of the data; and performing a control of contrast imaging for the object based on the trigger. The trigger is generated by a second threshold processing of data other than the abnormal data.

With reference to the accompanying drawings, an image diagnostic apparatus and a control method for the same according to an embodiment will now be described.

Figure 1:
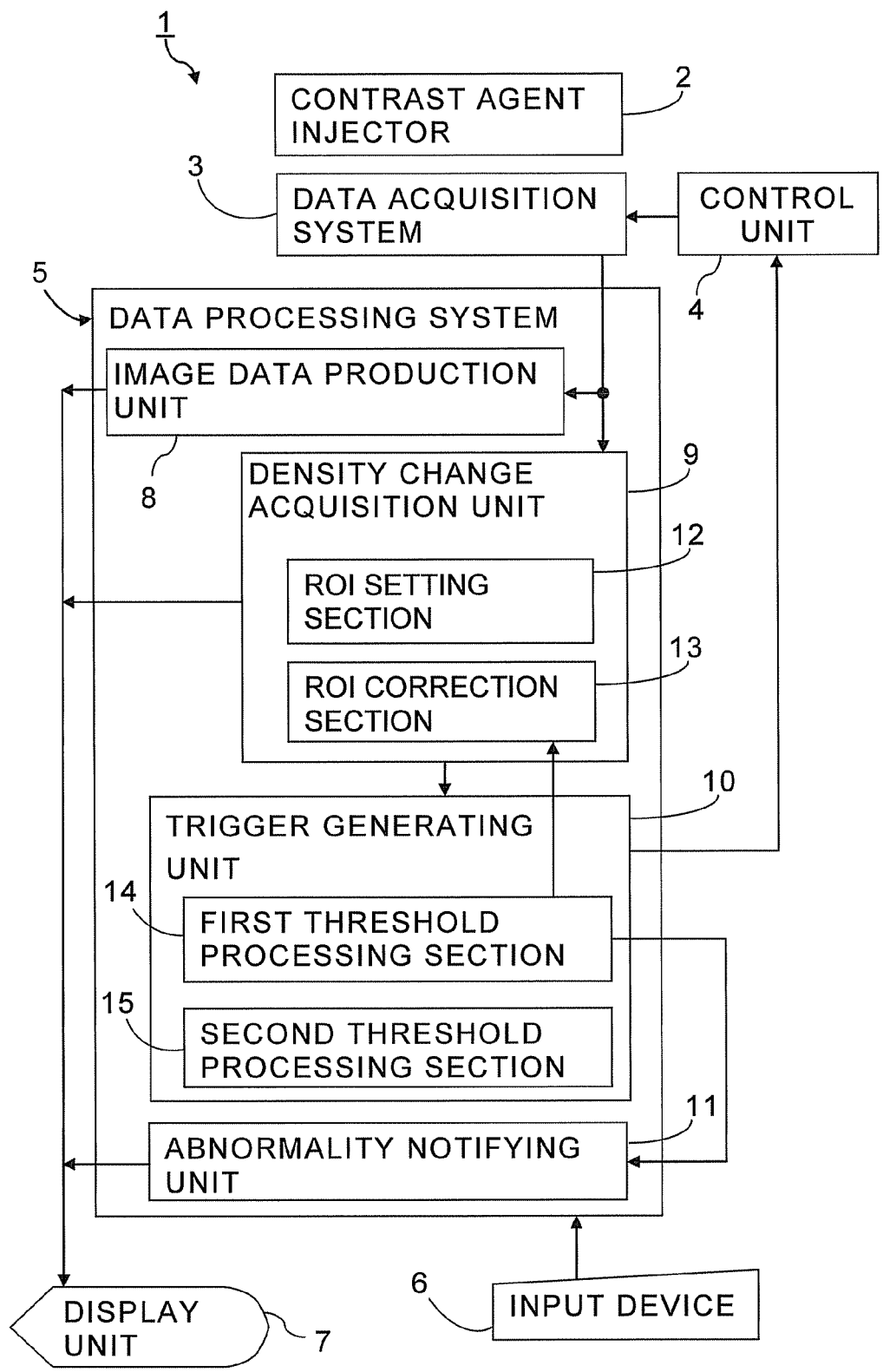
FIG. 1 is a block diagram functionally showing an image diagnostic apparatus according to an embodiment.

FIG. 1 functionally shows the configuration of an image diagnostic apparatus 1 according to the embodiment.

The image diagnostic apparatus 1 has functions for performing contrast imaging for an object. For such a purpose, this image diagnostic apparatus 1 includes a contrast agent injector 2, a data acquisition system 3, a control unit 4, a data processing system 5, an input device 6, and a display unit 7. Of such components of the image diagnostic apparatus 1, components necessary for processing digital data can be provided as a computer which has read programs assigned to the processing. The image diagnostic apparatus 1 can be exemplified as an X-ray CT (computed tomography) scanner or an MRI (magnetic resonance imaging) system which is capable of performing contrast imaging.

The contrast agent injector 2 has a function of bolus- or intravenous-injecting a contrast agent into an object.

The data acquisition system 3 has a function of acquiring biological data from the object by performing a scan based on predetermined conditions. When the image diagnostic apparatus 1 is provided as an X-ray CT scanner, the data acquisition system 3 is given as components including an X-ray tube and an X-ray detector, where such components acquire X-ray absorption data, as the biological data, from an object being diagnosed. Meanwhile when the image diagnostic apparatus 1 is provided as an MRI system, the data acquisition system 3 is given as components including coils and magnets, where such components acquire MR (magnetic resonance) data, as the biological data, from an object being diagnosed.

The control unit 4 is capable of controlling the data acquisition system 3 based on a trigger signal outputted from the data processing system 5, whereby the control unit 4 is given a function of enabling the data acquisition system 3 to perform an imaging scan and a pre-scan carried out prior to the imaging scan. The imaging scan is performed to acquire contrasted image data as an image diagnostic data. The pre-scan has various types of pre-scans, including a pre-scan performed to acquire image data on which ROIs are set and another pre-scan performed to monitor the density of a contrast agent flowing through an object's portion designated by a desired ROI. For such purposes, the control unit 4 has a function of setting ROIs on images in accordance with commands given through the input device 6.

The control unit 4 has additional functions including a function of controlling the data acquisition system 3 for the contrast imaging based on the trigger signal outputted from the data processing system 5 and a function of providing the display unit 7 and other devices with information necessary for the contrast imaging. For example, the control unit 4 has functions for changing imaging modes based on a trigger signal and outputting information. Specifically such functions include a function of outputting voice guidance when an index, such as CT values, showing a contrast effect within a ROI given to an object's image exceeds a given value; a function of controlling the data processing system 5 to prolong imaging intervals when the index showing the contrast effect exceeds a peak thereof; a function of controlling the data processing system 5 to reduce a tube current supplied to an X-ray tube when the index showing the contrast effect exceeds the peak; and a function of controlling the data processing system 5 to end the imaging when the index showing the contrast effect becomes equal to or less than the given value.

The data processing system 5 functionally includes an image data production unit 8, a density change acquisition unit 9, a trigger generating unit 10, and an abnormality notifying unit 11. The density change acquisition unit 9 functionally includes a ROI (region of interest) setting section 12 and a ROI correction section 13. Furthermore, the trigger generating unit 10 functionally includes a first threshold processing section 14 and a second threshold processing section 15.

The image data production unit 8 has two functions, one of which is to produce image data by applying an image reconstruction process to biological data acquired through an imaging scan or a pre-scan conducted by the data acquisition system 3. The other function is to make the display unit 7 display unit the produced image data.

The density change acquisition unit 9 also has two functions. One function is to acquire, as a TDC of a contrast agent, data showing temporal changes in the density of the contrast agent based on the biological data acquired by the pre-scan conducted by the data acquisition section 3. The other function is to enable the display unit 7 to display the TDC of the contrast agent.

For example, the image diagnostic apparatus 1 is realized as an X-ray CT scanner. In such a case, a TDC of a contrast agent is produced as changes in CT values calculated within a ROI which is set on an X-ray CT image. Alternatively the image diagnostic apparatus 1 can be realized as an MRI system, in which a TDC of a contrast agent is produced as changes in pixel values calculated within a ROI which is set on an MR image data or changes in signal values of MR signals acquired from a given region of an object.

The ROI setting section 12 complies with information from the input device 6 to have a function of setting a ROI for producing a TDC of the contrast agent. Since there are plural pixels in the ROI, a representative value, such as an average of values of the plural pixels or plural CT values, is used to prepare one TDC for each ROI. Accordingly, several ROIs may be set to prepare several TDCs.

The ROI correction section 13 has a function of performing a process of correcting a ROI. In this correction process, the ROI correction section 13 performs threshold processes, when an abnormal TDC is prepared, to thereby localize an area in which the data presents abnormal values. Further, in this correction process, the ROI correction section 13 excludes the area presenting abnormal values from the ROI and determines the area after exclusion as a new ROI. More specifically, the ROI correction section 13 performs the process of correcting a ROI. Owing to this, in the event that an abnormal TDC is prepared, the density change acquisition unit 9 is able to prepare a TDC using data of the area from which the area presenting abnormal values has been excluded. The information as to whether or not an abnormal TDC has been prepared is given from the first threshold processing section 14 of the trigger generating unit 10 to the ROI correction section 13.

The trigger generating unit 10 has a function of applying a first threshold process to a TDC of a contrast agent to detect abnormal data from the TDC. The trigger generating unit 10 also has a function of applying a second threshold process to the TDC, upon detection of abnormal data, to exclude the abnormal data from the TDC to thereby produce a trigger signal. The trigger generating unit 10 is configured not to necessarily produce a trigger signal whenever trigger signal producing conditions are met after applying the second threshold process to the TDC. For example, no trigger signal is produced if the data of the TDC targeted to the second threshold process is determined to be abnormal through the first threshold process. In other words, the first threshold process may be performed first, or the second threshold process may be performed first.

In addition, the trigger generating unit 10 has a function of outputting a produced trigger signal to the control unit 4. Being provided with a trigger signal, the control unit 4 is able to start scan, change imaging mode, or output necessary information.

The first threshold processing section 14 has a function of applying the first threshold process to a TDC to determine whether or not a local data in the TDC is abnormal. For example, the first threshold processing section 14 sets a first threshold for the values of a TDC of a contrast agent or for the variation rate of the TDC. When a value or the variation rate of a TDC exceeds the first threshold, the portion of the TDC, which portion exceeds the first threshold, is determined to be abnormal data. For example, the first threshold may be empirically determined based on abnormal values of TDCs detected in the past.

The second threshold processing section 15 has a function of applying a second threshold process to a TDC to determine the timing of producing a trigger signal. If the trigger signal is used for starting imaging scan, it is determined in the second threshold process that the conditions for producing the trigger signal are met when a value of the TDC exceeds the second threshold. Further, if the trigger signal is used for changing an imaging mode or for outputting information, a second threshold and the way of performing the second threshold process are determined according to the conditions for changing an imaging mode or the conditions for outputting information.

The second threshold may be set to an empirical value that has been used in the past for determining a timing for producing a trigger signal.

The following description is provided by way of an example. In the example, the second threshold processing section 15 determines conditions under which a trigger signal for starting imaging scan is produced, and the trigger generating unit 10 produces such a trigger signal for starting imaging scan.

Figure 2:
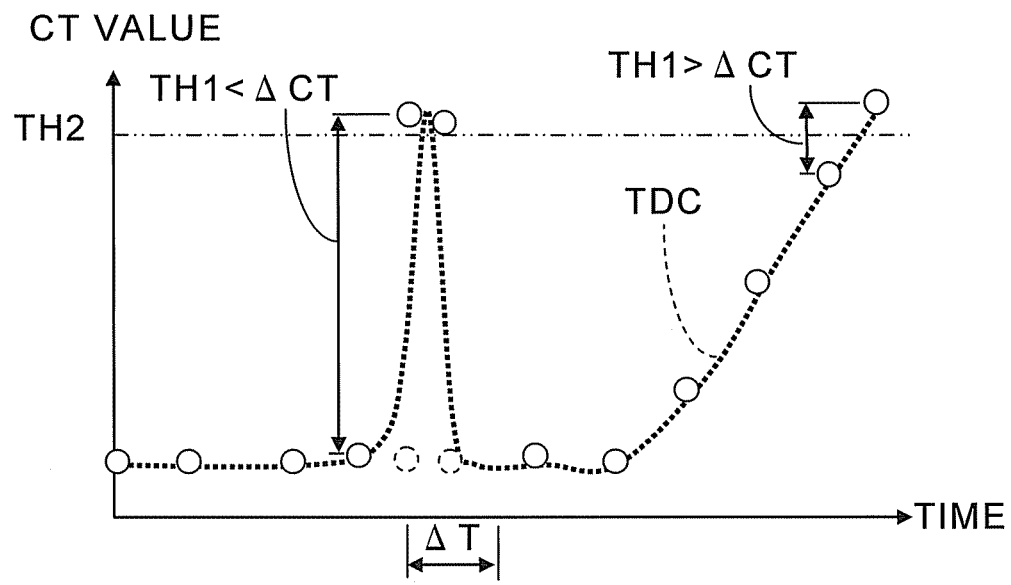
FIG. 2 is a graph explaining how to produce a trigger signal by applying first and second threshold processes to a time density curve (TDC) involving abnormal data.
Figure 3:
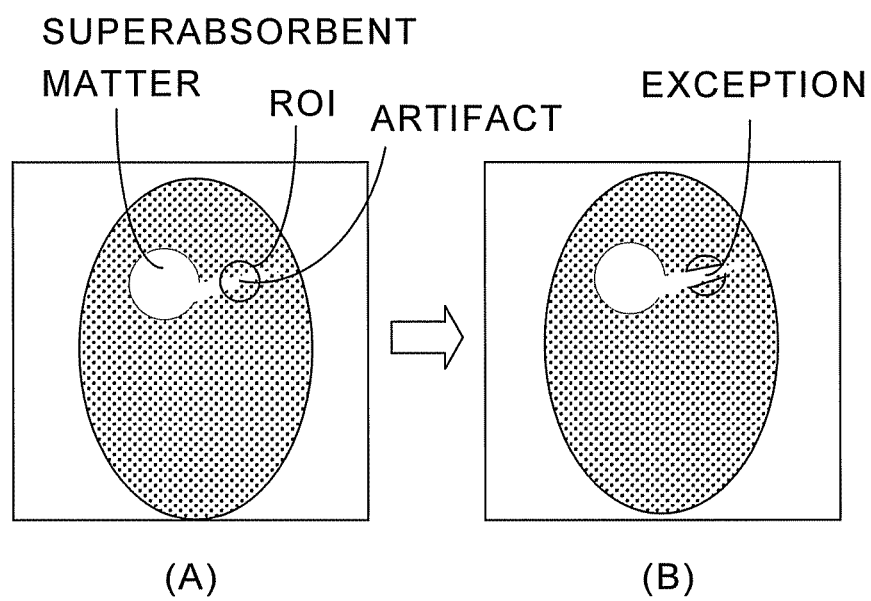
FIG. 3 is an illustration exemplifying exception of an area of pixels presenting abnormal values, from a ROI from which the TDC shown in FIG. 2 has been produced.

FIG. 2 is a graph explaining how to produce a trigger signal by applying first and second threshold processes to a TDC involving abnormal data. FIG. 3 is an illustration exemplifying an area after exclusion of pixels presenting abnormal values, from a ROI from which the TDC shown in FIG. 2 has been produced.

In FIG. 2, the horizontal axis shows time and the vertical axis shows CT values in a ROI. Further, the dotted line in FIG. 2 shows a TDC expressed as temporal changes of CT values in the ROI. The solid line circles show plots of CT values at individual sampling time points for producing the TDC.

As shown by (A) of FIG. 3, a ROI is set on an X-ray CT image, followed by injection of a contrast agent and pre-scan to thereby acquire X-ray detection data in a dynamic manner. In the meantime, CT values in the ROI are calculated in real time to acquire a TDC in the ROI. Thus, concentration of the contrast agent in the ROI is monitored in terms of a TDC.

The contrast agent gradually flows into the ROI. Therefore, if the TDC reflects the concentration of the contrast agent in the ROI, the TDC will not drastically rise or fall but will continuously and gradually rise. However, as shown by (A) in FIG. 3, if superabsorbent matter that absorbs X-rays extremely well is present in the proximity of the ROI, the superabsorbent matter may affect the ROI in the X-ray CT image to cause an artifact in the ROI. With the appearance of such an artifact in the ROI, the TDC will drastically rise and then drastically fall.

As shown in FIG. 2, a trigger signal of imaging scan is ensured to be produced when the TDC exceeds a second threshold TH2. Therefore, when the TDC drastically rises and exceeds the second threshold TH2 due to the appearance of the artifact, a trigger signal is unavoidably produced although the contrast agent has not yet reached and entered into the ROI.

As a measure against this, when a CT value on the TDC exceeds the second threshold TH2, a difference $\Delta CT$ of the CT value from the CT value sampled immediately before may be calculated. The difference $\Delta CT$ may then be compared with a first threshold TH1. If the difference $\Delta CT$ is larger than the first threshold TH1, the trigger generating unit 10 may be controlled so as not to produce a trigger signal. For example, when a ROI is set in a carotid artery, the first threshold TH1 may be set to about 30 HU (Hounsfield Unit).

Through such a first threshold process, a drastic change may be found in the difference $\Delta CT$ of a CT value from the TC value sampled immediately before, the difference being an index of the variation rate of a TDC. In this case, the rise of the TDC may be determined as having been caused by an artifact and then it is ensured that a trigger signal is not produced.

As a result of the comparison of the difference $\Delta CT$ of a CT value with the first threshold TH1 as described above, the difference $\Delta CT$ of the CT value may be determined to be equal to or smaller than the first threshold TH1. In this case, the CT value may be compared with the second threshold TH2 to make a determination. Also, the difference $\Delta CT$ of a CT value from the CT value sampled immediately before may be used as an index of the variation rate of the TDC. This may well contribute to the determination as to whether or not the cause of the rise of a CT value is ascribed to an artifact. Alternatively, values of an n number (n is a natural number) of CT values preceding a specified CT value may be averaged to calculate a difference between the specified CT value and the average value. The difference calculated in this way may be used as an index of the variation rate of the TDC and thus may be compared with the first threshold TH1.

However, as shown in FIG. 2, a drastic rise of a CT value due to an artifact may be followed by the subsequently sampled CT value that also exceeds the second threshold TH2. In this case, the difference $\Delta CT$ between these CT values is small.

In this regard, when the difference $\Delta CT$ between the specified CT value and a CT value sampled immediately before exceeds the first threshold TH1 and thus the specified CT value is determined to be abnormal, the trigger generating unit 10 may be controlled such that a trigger signal is not produced before lapse of at least a predetermined time $\Delta T$. The predetermined time $\Delta T$ may be empirically determined based such as on temporal data regarding the occurrence of abnormal data in the past.

As described above, the ROI correction section 13 localizes the area presenting abnormal CT values to exclude the area from the ROI as shown by (B) in FIG. 3. Thus, as shown by dotted circles in FIG. 2, such CT values are corrected to normal values. In this case, since the artifact has been excluded from within the ROI, the subsequently sampled CT value is also corrected to a normal value.

Controlling the trigger generating unit 10 in this way, imaging scan will not be started in the event abnormal data occurs in a TDC, but the pre-scan for monitoring the TDC can be continuously performed.

Then, as shown in FIG. 2, the TDC gradually rises in conformity with the concentration of the contrast agent. In the rise, when a CT value exceeds the second threshold TH2, the difference $\Delta CT$ from the CT value sampled immediately before becomes equal to or smaller than the first threshold TH1. Thus, a trigger signal is produced at an appropriate timing.

Figure 4:
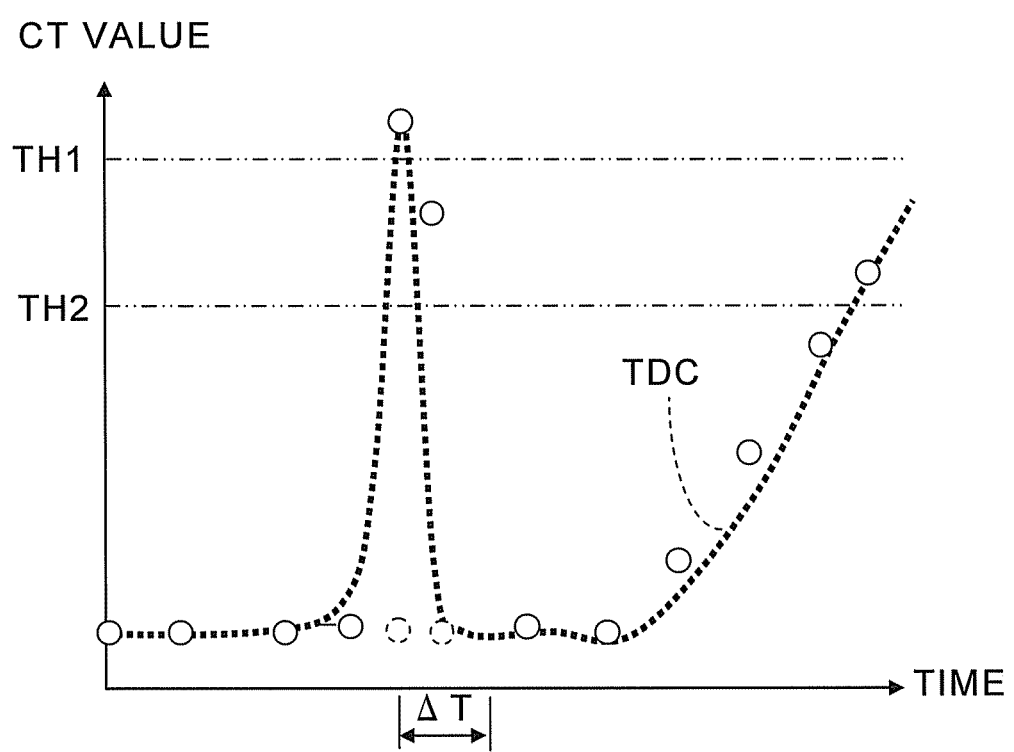
FIG. 4 is a graph explaining, as another way, how to produce a trigger signal by applying first and second threshold processes to a TDC involving abnormal data.

FIG. 4 is a graph explaining, as another way, how to produce a trigger signal by applying first and second threshold processes to a TDC involving abnormal data.

In FIG. 4, the horizontal axis shows time and the vertical axis shows CT values in a ROI. The dotted line in FIG. 4 shows a TDC expressing temporal changes of CT values in the ROI. The solid line circles show plots of CT values at individual sampling time points for producing the TDC.

As shown in FIG. 4, a first threshold TH1 and a second threshold TH2 may be set for the CT values composing the TDC. The first threshold TH1 is used for excluding abnormal values. The second threshold TH2 is used for determining conditions for producing a trigger signal. Specifically, a CT value, per se, may be used as an index of the variation rate of the TDC in performing a first threshold process. In this case, the first threshold TH1 is set to a value well exceeding the second threshold TH2 and well exceeding an expected value to which the TDC would rise due to the arrival of the contrast agent. Thus, when a CT value exceeds the second threshold TH2 due to an artifact, no trigger signal is produced on condition that the CT value also exceeds the first threshold value.

The trigger generating unit 10 may be controlled so that a trigger signal is not produced before lapse of at least a predetermined time $\Delta T$ in the case: where a portion corresponding to an artifact is excluded from a ROI to correct CT values as shown by dotted circles in FIG. 4; or where CT values are determined to be abnormal.

The abnormality notifying unit 11 has a function of having the display unit 7 displayed information of having detected abnormal data when the abnormal data is detected in the first threshold processing section 14. Specifically, the abnormality notifying unit 11 has a function of notifying the user of information such as the information that the rise of the TDC is caused by artifacts.

Hereinafter are described advantages and effects of the image diagnostic apparatus 1. The image diagnostic apparatus 1 here is an X-ray CT scanner. The following description is given taking as an example the case where the first and second threshold processes shown in FIG. 2 are performed to produce a trigger signal for imaging scan.

Figure 5:
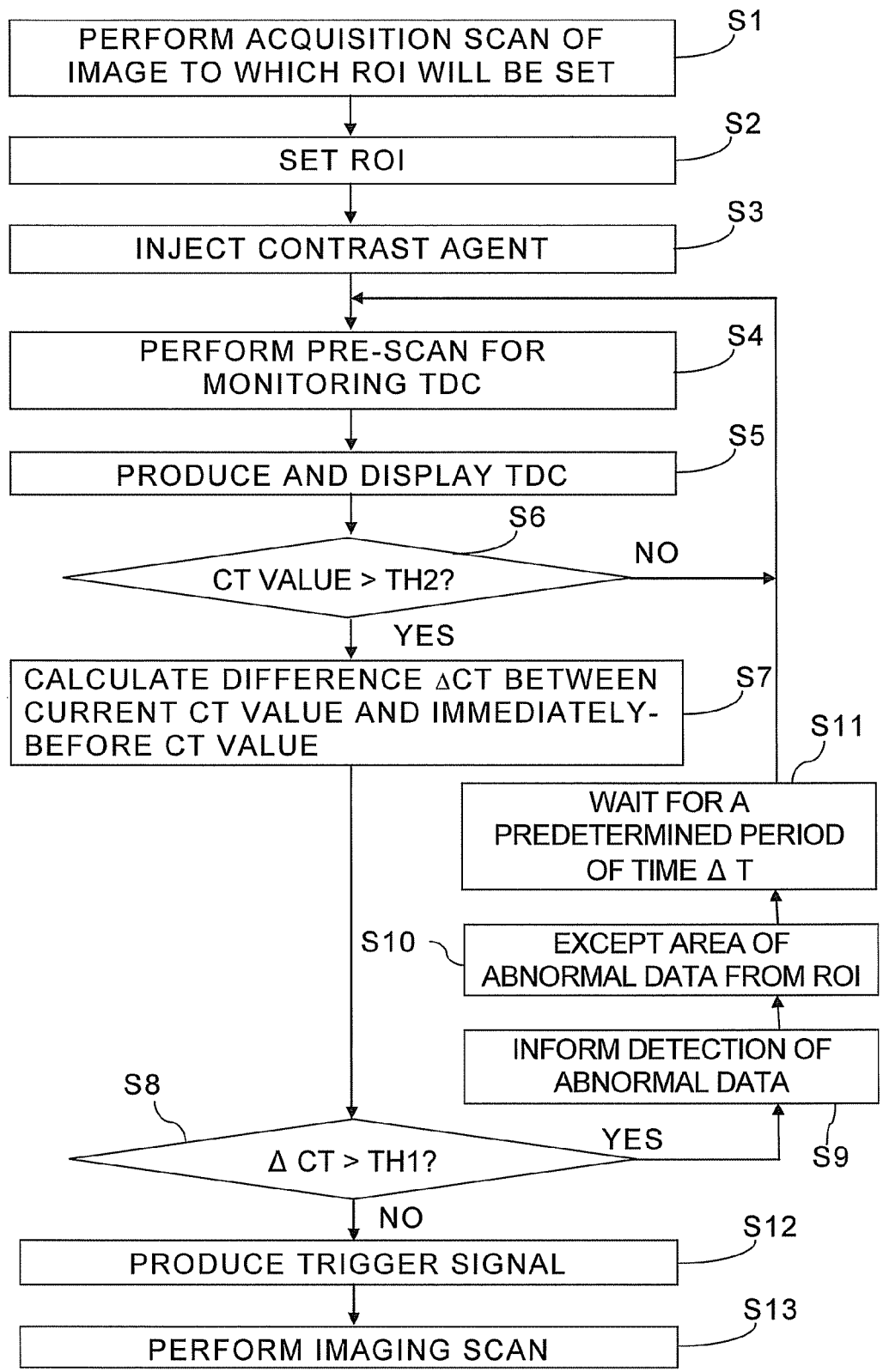
FIG. 5 is a flowchart showing a flow of contrast imaging for an object, which imaging is performed at a timing which has been set through monitoring a TDC of a contrast agent by using the image diagnostic apparatus shown in FIG. 1.

FIG. 5 is a flowchart showing a flow of contrast imaging for an object, which imaging is performed at a timing which has been set through monitoring a TDC of a contrast agent by using the image diagnostic apparatus shown in FIG. 1.

At step S1 in FIG. 5, first, pre-scan is performed to acquire image data for setting a ROI for which a TDC of a contrast agent is prepared. Specifically, under the control of the control unit 4, the data acquisition system 3 performs pre-scan of a desired mode, such as an S & S (scan & scan) mode, S & V (scan & view) mode, helical scan mode or volume scan mode. With the pre-scan, X-ray detection data in a site, i.e. a target of examination, of the object is acquired.

More specifically, X-rays are radiated to the object from an X-ray tube provided in the data acquisition system 3. The X-ray transmitted through the object is detected by an X-ray detector. The X-ray detected by the X-ray detector is acquired, as data, by a data acquisition system (DAS). The X-ray detection data is outputted as a digital signal from the DAS to the data processing system 5.

Then, the image data production unit 8 of the data processing system 5 carries out an image reconstruction process for the X-ray detection data. Through the image reconstruction process, image data is produced, which is then displayed on the display unit 7.

Then, at step S2, the ROI setting section 12 sets a ROI based on the information from the input device 6, so that a TDC of a contrast agent is prepared for the ROI. Specifically, the user refers to the image displayed on the display unit 7 and operates the input device 6 to input the ROI setting information to the ROI setting section 12. Then, the ROI setting section 12 sets a ROI, as shown by (A) in FIG. 3, according to the ROI setting information.

Then, at step S3, the contrast agent injector 2 injects a contrast agent into the object.

Then, at step S4, the data acquisition system 3 carries out pre-scan for monitoring a TDC of the contrast agent injected to the object, under the control of the control unit 4. Specifically, in a flow similar to that of step S1, X-ray detection data is outputted from the DAS to the data processing system 5. However, the X-ray detection data is dynamically acquired in the pre-scan for monitoring a TDC.

Then, at step S5, the density change acquisition unit 9 of the data processing system 5 produces X-ray CT image data in real time through the image reconstruction process of the X-ray detection data to measure CT values in the ROI in the X-ray CT image data. Then, the density change acquisition unit 9 prepares a TDC of the contrast agent, reflecting temporal changes of CT values in the ROI, and displays the prepared TDC of the contrast agent on the display unit 7.

Alternative to displaying the TDC of the contrast agent on the display unit 7, the density change acquisition unit 9 may store CT values obtained at individual sampling time points.

Then, at step S6, the second threshold processing section 15 performs applies the second threshold process to the TDC to determine a timing for producing a trigger signal. Specifically, the second threshold processing section 15 determines whether or not the latest CT value sampled in the ROI has exceeded the predetermined second threshold TH2. If the CT value is determined as not exceeding the second threshold TH2, control returns to step S4 to continuously perform the pre-scan for monitoring the TDC to obtain a TDC of the contrast agent.

On the other hand, if an artifact appears in the X-ray CT image data due to the influence of a superabsorbent matter which is located in the proximity of the ROI and well absorbs X-ray, CT values drastically increases. Therefore, it may be determined that the CT value has exceeded the second threshold TH2.

Then, at step S7, the first threshold processing section 14 calculates the difference $\Delta$CT between the CT value determined as exceeding the second threshold TH2 and the CT value sampled immediately before the CT value in question.

Then, at step S8, the first threshold processing section 14 applies the first threshold process to the difference $\Delta$CT of the CT value. This process is performed for the purpose of determining whether or not the CT value exceeding the second threshold TH2 is abnormal due to the presence of an artifact. Specifically, the first threshold processing section 14 determines whether or not the difference $\Delta$CT of the CT value has exceeded the predetermined first threshold TH1.

Then, if it is determined that the difference $\Delta$CT of the CT value has exceeded the first threshold TH1, control returns to step S4 to continuously perform the pre-scan for monitoring the TDC and to obtain a TDC of the contrast agent. Thus, in the event that a CT value exceeds the second threshold TH2 due to an artifact, the difference $\Delta$CT of the CT value that has drastically changed due to the artifact exceeds the first threshold TH1. Accordingly, the pre-scan for monitoring the TDC is continuously performed.

As necessary, at step S9, the first threshold processing section 14 gives the information of having detected abnormal data to the abnormality notifying unit 11. The abnormality notifying unit 11 displays the information of occurring abnormal data on the display unit 7, e.g. the information that the rise of the TDC is due to an artifact. Thus, the user is able to confirm that the rise of CT values is caused by the artifacts.

Further, as necessary, at step S10, the ROI correction section 13 performs the first threshold process to localize an area in the ROI, in which a CT value shows abnormality. For example, such an area corresponds to an area of pixels, in which a CT value exceeds the second threshold TH2, or an area of pixels, in which the difference $\Delta$CT of a CT value exceeds the first threshold TH1. Then, as shown by (B) in FIG. 3, the ROI correction section 13 performs the correction process to exclude the localized area presenting abnormal data from the ROI. Thus, a CT value sampled from the corrected ROI presents a normal value, without being affected by artifacts.

Further, as necessary, at step S11, the trigger generating unit 10 stands by until the predetermined time $\Delta$T elapses. Thus, the drastic rise of CT values due to an artifact comes to an end and CT values again show normal values.

Steps S9, S10 and S11 may be independently performed in no particular order.

On the other hand, when the contrast agent reaches the ROI and enters therein, CT values gradually increase and exceed the second threshold TH2. In this case, at step S8, the first threshold processing section 14 determines that the difference $\Delta$CT of a CT value does not exceed the first threshold TH1.

In this case, at step S12, the trigger generating unit 10 produces a trigger signal that provides a timing for starting imaging scan, and outputs the produced trigger signal to the control unit 4.

Then, at step S13, upon receiving the trigger signal, the control unit 4 controls the data acquisition system 3 to have it performed the contrast imaging scan. Thus, contrast CT image data reflecting the ROI stained and contrasted by the contrast agent is acquired as an image diagnostic data.

As described above, the first threshold process for detecting abnormal data may be performed prior to the second threshold process for determining conditions for producing a trigger signal.

The image diagnostic apparatus 1 described above applies the first threshold process to the TDC of a contrast agent to determine whether or not the changes of the TDC are ascribed to the contrast agent or other factors. Then, only when the TDC rises or falls due to the contrast agent, the imaging scan is started, the imaging mode is changed, or a trigger signal is produced for determining output of information.

Thus, the image diagnostic apparatus 1 is able to avoid inappropriate setting of a timing for starting the contrast imaging scan, a timing for changing an imaging mode, or a timing for outputting information, in the event that the data for monitoring the concentration of a contrast agent rises or falls due to factors other than the contrast agent. In other words, the image diagnostic apparatus 1 is able to produce a trigger signal at an appropriate timing, for controlling the contrast imaging scan.

For example, if an artifact appears in contrast X-ray CT image data acquired by an X-ray CT scanner, a portion of the TDC, which has risen due to the appearance of the artifacts is excluded to produce a trigger signal at an appropriate timing.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutes and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image diagnostic apparatus comprising:
a computer configured to
acquire data corresponding to a temporal change in density of a contrast agent injected into an object,
determine a timing for producing a trigger by a second threshold processing for the acquired data other than abnormal data,
prevent the trigger from being finally produced when the abnormal data has been detected by a first threshold processing in the acquired data,
produce the trigger when no abnormal data has been detected by the first threshold processing in the acquired data, wherein the second threshold processing includes a comparison of a CT value or a pixel value and a predetermined second threshold value while the first threshold processing includes a comparison of a chronological change in two adjacent CT values or pixel values and a predetermined first threshold value, and
perform a control of contrast imaging for the object based on the trigger, wherein a control target for the contrast imaging is the image diagnostic apparatus including an X-ray CT scanner or a MRI system.

2. An image diagnostic apparatus of claim 1, wherein said computer is configured to acquire a certain portion of the acquired data corresponding to the temporal change in the density of the contrast agent from a region of interest excluding a region corresponding to the abnormal data when the abnormal data has been detected.

3. An image diagnostic apparatus of claim 1, wherein said computer is configured to prevent the trigger from being finally produced after at least a predetermined period has elapsed when the abnormal data has been detected.

4. An image diagnostic apparatus of claim 1, wherein said computer is configured to perform the contrast imaging of the object using the trigger as a start time for the contrast imaging.

5. An image diagnostic apparatus of claim 1, wherein said computer is configured to cause a display to display information relating to detecting the abnormal data when the abnormal data has been detected.

6. A method of controlling an image diagnostic apparatus, comprising:
acquiring data corresponding to a temporal change in density of a contrast agent injected into an object;
determine a timing for producing a trigger by a second threshold processing for the acquired data other than abnormal data;
preventing the trigger from being finally produced when the abnormal data has been detected by a first threshold processing in the acquired data;
producing the trigger when no abnormal data has been detected by the first threshold processing in the acquired data, wherein the second threshold processing includes a comparison of a CT value and a predetermined second threshold value or a pixel value while the first threshold processing includes a comparison of a chronological change in two adjacent CT values or pixel values and a predetermined first threshold value; and
performing a control of contrast imaging for the object based on the trigger, wherein a control target for the contrast imaging is the image diagnostic apparatus including an X-ray CT scanner or a MRI system.

7. An image diagnostic apparatus comprising:
a computer further comprising:
a density change acquisition unit configured to acquire data corresponding to a temporal change in density of a contrast agent injected into an object;
a trigger generating unit configured to determine a timing for producing a trigger by a second threshold processing for the acquired data other than the abnormal data, to prevent the trigger from being finally produced when abnormal data has been detected by a first threshold processing in the acquired data, and to produce the trigger when no abnormal data has been detected by the first threshold processing in the acquired data, wherein the second threshold processing includes a comparison of a CT value or a pixel value and a predetermined second threshold value while the first threshold processing includes a comparison of a chronological change in two adjacent CT values or pixel values and a predetermined first threshold value; and
a control unit configured to perform a control of contrast imaging for the object based on the trigger, wherein a control target for the contrast imaging is the image diagnostic apparatus including an X-ray CT scanner or a MRI system.

\* \* \* \* \*